US007540871B2

(12) United States Patent
Gonnering (10) Patent No.: US 7,540,871 B2
(45) Date of Patent: Jun. 2, 2009

(54) INTEGRATED THREE-PORT RECEPTACLE AND METHOD FOR CONNECTING HAND AND FOOT SWITCHED ELECTROSURGICAL ACCESSORIES

(75) Inventor: Wayne J. Gonnering, Littleton, CO (US)

(73) Assignee: ConMed Corporation, Utica, NY (US)

( * ) Notice: Subject to any disclaimer, the term of this patent is extended or adjusted under 35 U.S.C. 154(b) by 841 days.

(21) Appl. No.: 11/195,976

(22) Filed: Aug. 3, 2005

(65) Prior Publication Data
US 2007/0032789 A1 Feb. 8, 2007

(51) Int. Cl.
*A61B 18/04* (2006.01)
(52) U.S. Cl. .................. 606/34; 439/638; 439/909; 607/2; 606/41
(58) Field of Classification Search ............. 606/42, 606/45, 49, 32–35, 37–40, 48, 50; 439/246, 439/628, 638, 631
See application file for complete search history.

(56) References Cited

U.S. PATENT DOCUMENTS

| 4,463,759 | A | * | 8/1984 | Garito et al. .............. 606/42 |
| 5,562,503 | A | * | 10/1996 | Ellman et al. .............. 439/638 |
| 6,113,596 | A | * | 9/2000 | Hooven et al. ............. 606/42 |
| 6,685,703 | B2 | * | 2/2004 | Pearson et al. ............. 606/41 |
| 6,830,569 | B2 | * | 12/2004 | Thompson et al. ......... 606/34 |
| 6,835,082 | B2 | * | 12/2004 | Gonnering ................ 439/218 |
| 7,094,231 | B1 | * | 8/2006 | Ellman et al. .............. 606/37 |
| 7,131,860 | B2 | * | 11/2006 | Sartor et al. ............... 439/489 |
| 7,416,437 | B2 | * | 8/2008 | Sartor et al. ............... 439/489 |
| 2004/0097916 | A1 | * | 5/2004 | Thompson et al. ......... 606/34 |
| 2006/0079871 | A1 | * | 4/2006 | Plaven et al. .............. 606/34 |
| 2006/0217700 | A1 | * | 9/2006 | Garito et al. .............. 606/34 |

FOREIGN PATENT DOCUMENTS

WO WO 98/29044 7/1998

OTHER PUBLICATIONS

PCT/US 2006/029776, PCT International Search Report, dated Jan. 23, 2007.
PCT/US 2006/029776, PCT Written Opinion of the International Searching Authority, dated Jan. 23, 2007.
WO 00/22996, published Apr. 27, 2000, PCT/US 99/11640, filed May 26, 1999.
WO 98/29044, published Jul. 9, 1998, PCT/US 97/24157, filed Dec. 19, 1997.
PCT International Preliminary Report on Patentability with attached Written Opinion of the International Searching Authority for International Application No. PCT/US2006/029776, dated Feb. 5, 2008, 6 pages.

* cited by examiner

*Primary Examiner*—Terrell L McKinnon
*Assistant Examiner*—Amanda Scott
(74) *Attorney, Agent, or Firm*—John R. Ley (57) ABSTRACT

A three-port receptacle connects both single-prong and three-prong electrical connectors of electrosurgical accessories to an electrosurgical generator. The receptacle includes two control ports for accepting the two control prongs of the three-prong connector and an energy-delivery port for accepting the energy-conducting prong of the three-prong connector. The energy-delivery port also receives an energy-conducting prong of a single-prong connector. A single contact assembly is located behind the energy-delivery port and delivers electrosurgical power to the energy-conducting prongs of both types of accessory connectors.

27 Claims, 9 Drawing Sheets

INTEGRATED THREE-PORT RECEPTACLE AND METHOD FOR CONNECTING HAND AND FOOT SWITCHED ELECTROSURGICAL ACCESSORIES

This invention generally relates to electrosurgery, and more specifically, to a new and improved receptacle and method for electrically and mechanically connecting either a three-prong electrical connector of a hand-switched monopolar electrosurgical accessory or a single-prong electrical connector of a foot-switched monopolar electrosurgical accessory to an electrosurgical generator by use of an integrated three-port receptacle.

BACKGROUND OF THE INVENTION

Electrosurgery involves applying relatively high voltage, radio frequency (RF) electrical current to cut tissue, to coagulate or stop blood flow from tissue, or both to cut and coagulate tissue simultaneously. The electrosurgical energy of the high voltage, RF electrical current is created by an electrosurgical generator. The electrosurgical energy is applied to the tissue with an accessory or instrument connected to the electrosurgical generator. Electrical characteristics of the applied electrosurgical energy determines whether cutting, coagulating or simultaneous cutting and coagulating occurs.

In monopolar electrosurgery, the accessory has a single active electrode from which the electrosurgical energy is applied to the tissue at a surgical site to achieve the cutting, coagulating or simultaneous cutting and coagulating effects. The electrical current flows from the single active electrode through the patient to a single, relatively large, return electrode connected to the patient at a location remote from the surgical site. The return electrode collects the current from the patient's body and returns it to the electrosurgical generator, thereby completing an electrical circuit through the patient.

The delivery of electrosurgical energy to the accessory is controlled by the surgeon depressing or closing a switch on a handpiece of a finger switched accessory or by stepping on a foot switch located on the floor to deliver energy to a foot switched accessory. The handpiece of a finger switched accessory typically includes two finger switches, one for delivering electrosurgical energy for cutting and the other for delivering electrosurgical energy for coagulation. When using a foot switched accessory, closing the foot switch delivers the type of electrosurgical energy which the surgeon has selected from the front panel controls of the electrosurgical generator.

A three-prong electrical connector is used to connect a finger-switched monopolar accessory to the electrosurgical generator. One of the prongs conducts the electrosurgical energy to the active electrode. A second prong conducts a cut activation signal to the electrosurgical generator to cause it to deliver the cutting electrosurgical energy. A third prong conducts a coagulation activation signal to the electrosurgical generator to cause it to deliver the coagulating electrosurgical energy. The front panel of the electrosurgical generator includes a receptacle by which to connect the three-prong electrical connector to the electrosurgical generator. Three ports of the receptacle each receive one each of the prongs of the three-prong connector. The size and spacing of the ports and the prongs is standardized, so that a common finger-switched monopolar accessory can be connected to and used with a common electrosurgical generator.

A single-prong electrical connector is typically used to connect a foot-switched monopolar accessory to the electrosurgical generator. The single prong conducts the electrosurgical energy to the monopolar instrument, in response to the closure of the foot switch. The single prong is considerably larger than any of the three prongs associated with a three-prong electrical connector. The typical type of single-prong electrical connector is a Bovie #12 connector, which is standardized in size and shape for use with an electrosurgical generator. The foot switch is separately connected to the electrosurgical generator with its own connector that is usually located on a back panel of the generator.

Because of the differences in size and configuration of the three-prong electrical connector for a finger-switched accessory compared to the single-prong electrical connector for a foot-switched accessory, separate receptacles for connecting both types of connector are provided on most electrosurgical generators. Providing at least one receptacle for each type of monopolar accessory consumes valuable space on the front panel of the electrosurgical generator. The front panel must present various switches, selectors and displays used to operate and control the electrosurgical generator. The size of the front panel is typically dictated by the usual and expected dimensions for the electrosurgical generator, which must fit onto a cart and into other standard support equipment typically used in a surgical operating room. More advanced electrosurgical generators usually provide multiple receptacles for both the three-prong and the single-prong electrical connectors on the front panel to accommodate the simultaneous use of multiple monopolar accessories. One surgeon may use one or more monopolar accessories on an alternating basis during a single surgical procedure, or multiple surgeons may perform procedures simultaneously at separate surgical sites on the same patient while using their own monopolar accessories. An electrosurgical generator should not have only one three-prong receptacle or only one single-prong receptacle because a surgeon may have a preference for either finger-switched or foot-switched accessories and the provision of only one type of receptacle would not universally accommodate all the preferences of all surgeons.

An electrosurgical generator which is presently in use has a single receptacle within which there are four ports. One of the ports receives the single-prong electrical connector of the foot-switched accessory, and the other three ports receive the three prongs of the electrical connector of the finger-switched accessory. All four ports are integrated into approximately the same amount of front panel space normally consumed by a receptacle for the three-prong electrical connector. This four-port integrated receptacle conserves front panel space by allowing the three-prong electrical connector of a finger-switched electrosurgical accessory or the single-prong electrical connector of a foot-switched accessory to be connected in the space normally consumed by only one receptacle. However, the four-port receptacle does not simplify or reduce the size of the internal electrical connections of the electrosurgical generator. One port of the four-port receptacle delivers electrosurgical energy to an energy-conducting prong of the three-prong electrical connector, and another port of the four-port receptacle delivers electrosurgical energy to an energy-conducting prong of the single-prong electrical connector. The other two ports connect with control prongs of the three-prong electrical connector electrically connect the two finger switches to the electrosurgical generator.

Each of the two separate energy-delivery ports in this previous integrated four-port receptacle has its own separate electrical contact and its own separate energy-delivery relay. Closing the energy-delivery relay conducts the electrosurgical energy to the energy-conducting prong. Each energy-delivery relay must be separately controlled, according to the type of electrical connector inserted into the receptacle. Using two separate energy-delivery relays and two separate electrical contact assemblies, one for each energy-delivery port, increases the number of components, the complexity of the components, the amount of wiring and control circuits and logic required to deliver the electrosurgical energy to the energy-delivery port appropriate for the type of electrical connector connected to the generator. In this situation, the number of components used and housed within the interior of the electrosurgical generator is the same as if two separate and non-integrated receptacles are provided. More components consume more interior space and discourage attempts to reduce the size of the electrosurgical generator. The size, complexity and cost of the electrosurgical generator is not materially decreased by the four-port receptacle.

SUMMARY OF THE INVENTION

The present invention provides an integrated three-port receptacle by which to connect, to an electrosurgical generator, either a three-prong electrical connector of a finger-switched monopolar electrosurgical accessory or a single-prong electrical connector of a foot-switched monopolar electrosurgical accessory. One of the three ports delivers the electrosurgical energy to the energy-conducting prong of the three-prong electrical connector and to the energy-conducting prong of the single-prong electrical connector, depending on which type of electrical connector is attached to the electrosurgical generator. The energy-delivery port has a size capable of accepting either the relatively smaller energy-conducting prong of the three-prong electrical connector or the relatively larger energy-conducting prong of the single-prong electrical connector. To accept the relatively larger energy-conducting prong of the single-prong electrical connector, the single energy-delivery port of the integrated three-port receptacle must be made considerably larger than necessary to accommodate the relatively smaller energy-conducting prong of the three-prong electrical connector. A single internal contact assembly electrically connects to and contacts either type of energy-conducting prong. The use of a single internal contact assembly permits the use of a single power-delivery relay, thereby simplifying the amount of internal wiring, conductors and logic required to conduct the electrosurgical energy to either type of energy-conducting prong of either type of electrical connector. The consumption of internal space within the electrosurgical generator is reduced, because only one power delivery relay is required, among other things. Reducing the amount of internal space consumed in the electrosurgical generator may contribute to reducing the overall size of the electrosurgical generator, or may facilitate including more functional components on the front panel of or within the electrosurgical generator. Because only three ports in the integrated receptacle are available to connect the electrical connectors, it is virtually impossible for a user to attempt to connect incorrectly either the three-prong electrical connector or the single-prong electrical connector.

These and other beneficial features of the present invention are realized in and through the integrated three-port receptacle. The integrated three-port receptacle includes first and second control ports for receiving and electrically connecting control prongs of the three-prong electrical connector to the electrosurgical generator. The receptacle also includes an energy-delivery port for receiving an energy-conducting prong of a single-prong electrical connector and an energy-conducting prong of the three-prong electrical connector, on an alternative basis. The receptacle also includes an electrical contact, preferably in the form of an energy-delivery electrode, for contacting and electrically connecting to the energy-conducting prong of either of the three-prong connector or the single-prong electrical connector to deliver electrosurgical energy from the electrosurgical generator through the electrical connector to the electrosurgical accessory.

Another aspect of the invention involves a method of electrically connecting an electrosurgical accessory to the electrosurgical generator. The method includes inserting an energy-conducting prong of a three-prong electrical connector into an energy-delivery port of the electrosurgical generator to electrically connect the three-prong electrical connector to the electrosurgical generator, and also on an alternative basis, inserting an energy-conducting prong of a single-prong electrical connector into the same energy-delivery port of the electrosurgical generator to electrically connect the single-prong electrical connector to the electrosurgical generator. Two control prongs of the three-prong electrical connector are inserted into control ports, and the energy-conducting prong of the three-prong electrical connector is frictionally retained in the energy-delivery port by inserting the two control prongs of the three-prong electrical connector in the control ports. The energy-conducting prong of the single-prong electrical connector is frictionally retained in the energy-delivery port.

Other preferable aspects of the invention are as follows. The energy-conducting prong of the single-prong electrical connector is larger in a transverse dimension than the energy-conducting prong of the three-prong electrical connector is in a transverse dimension. The energy-delivery port has a fixed size which provides a relatively lesser clearance relative to the energy-conducting prong of the single-prong electrical connector and also provides a relatively greater clearance relative to the energy-conducting prong of the three-prong electrical connector. Contact with the energy-conducting prong is through an energy-delivery electrode which has an elongated contact arm portion that pivots relative to the energy-delivery port to move into contact with the energy-conducting prong, either on a distal end of the energy-conducting prong of the three-prong electrical connector or one a side wall of the energy-conducting prong of the single-prong electrical connector. The movement of the end portion of the contact arm portion into an indention in the side wall of the energy-conducting prong frictionally retains the single-prong electrical connector within the energy-delivery port.

A more complete appreciation of the invention and its scope, and the manner in which it achieves the above noted and other improvements, can be obtained by reference to the following detailed description of a presently preferred embodiment taken in connection with the accompanying drawings, which are briefly summarized below, and by reference to the appended claims.

DETAILED DESCRIPTION

Figure 1:
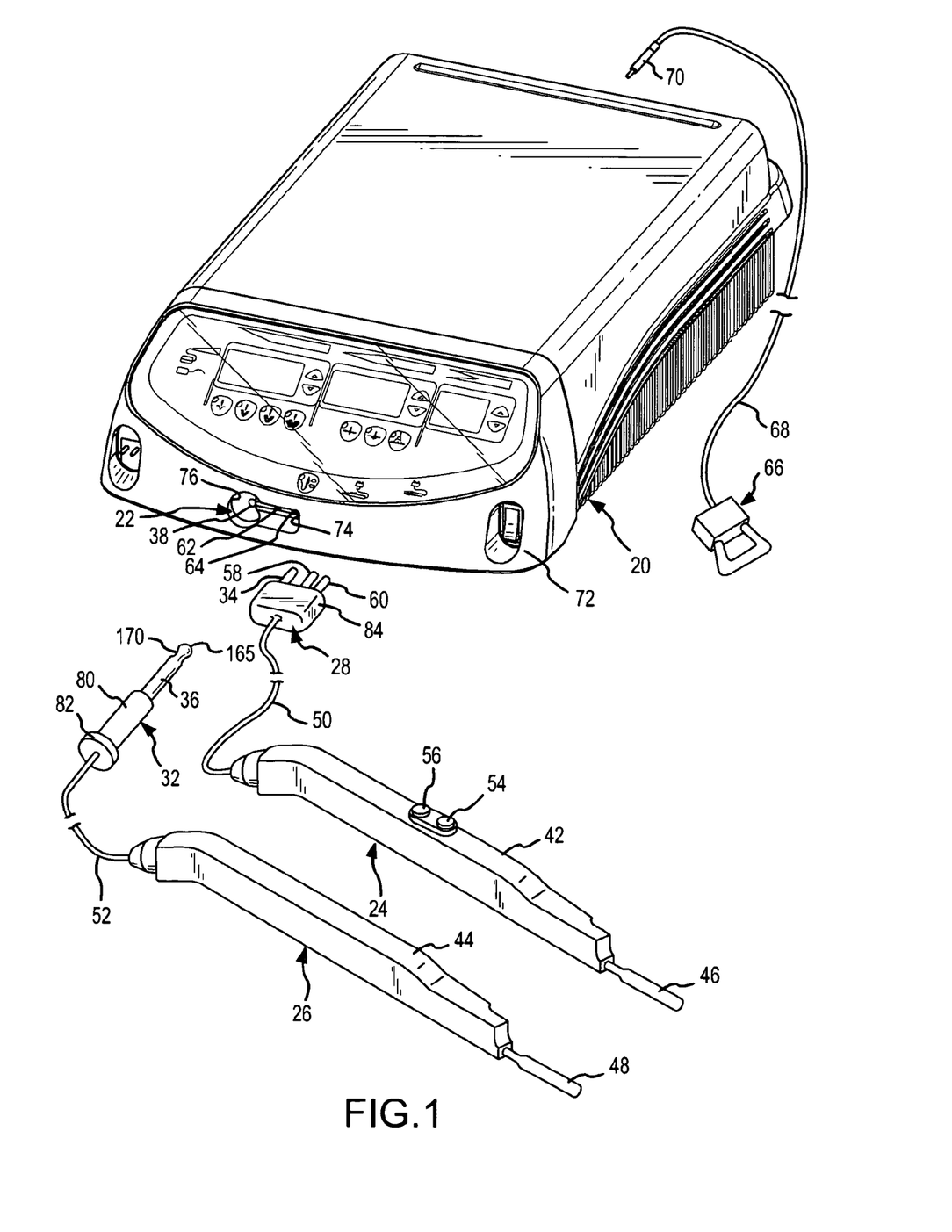
FIG. 1 is a front perspective view of an electrosurgical generator, a three-prong electrical connector of a hand-switched monopolar electrosurgical accessory and a single-prong electrical connector of a foot-switched monopolar electrosurgical accessory, either of which may be connected on an alternative basis to an integrated three-port receptacle of the electrosurgical generator in accordance with the present invention.
Figure 3:
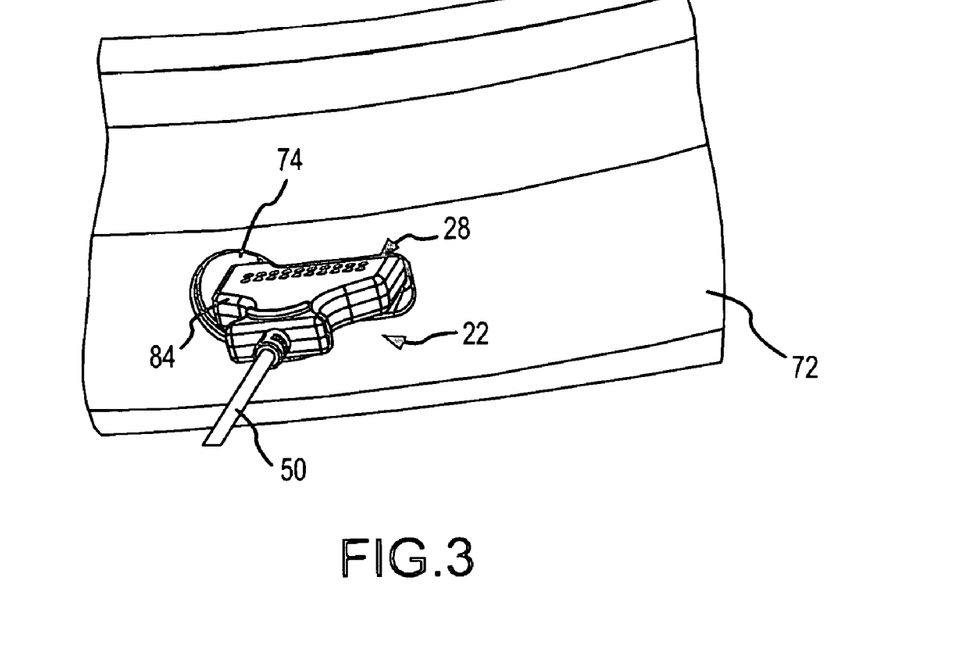
FIG. 3 is a front perspective view of a three-prong electrical connector of the hand-switched accessory shown in FIG. 1 inserted into the integrated three-port receptacle shown in FIG. 2.
Figure 4:
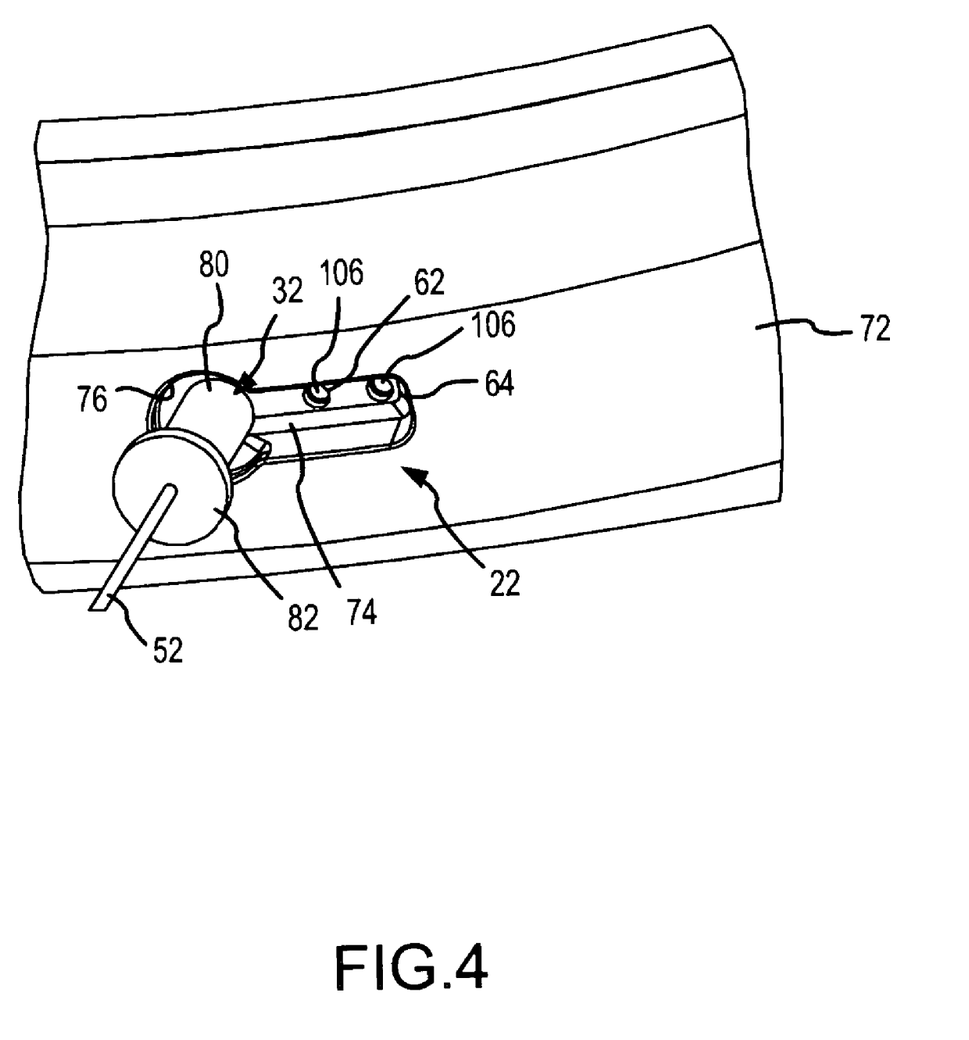
FIG. 4 is a front perspective view of a single-prong electrical connector of the foot-switched accessory shown in FIG. 1 inserted into the integrated three-port receptacle shown in FIG. 2.
Figure 10:
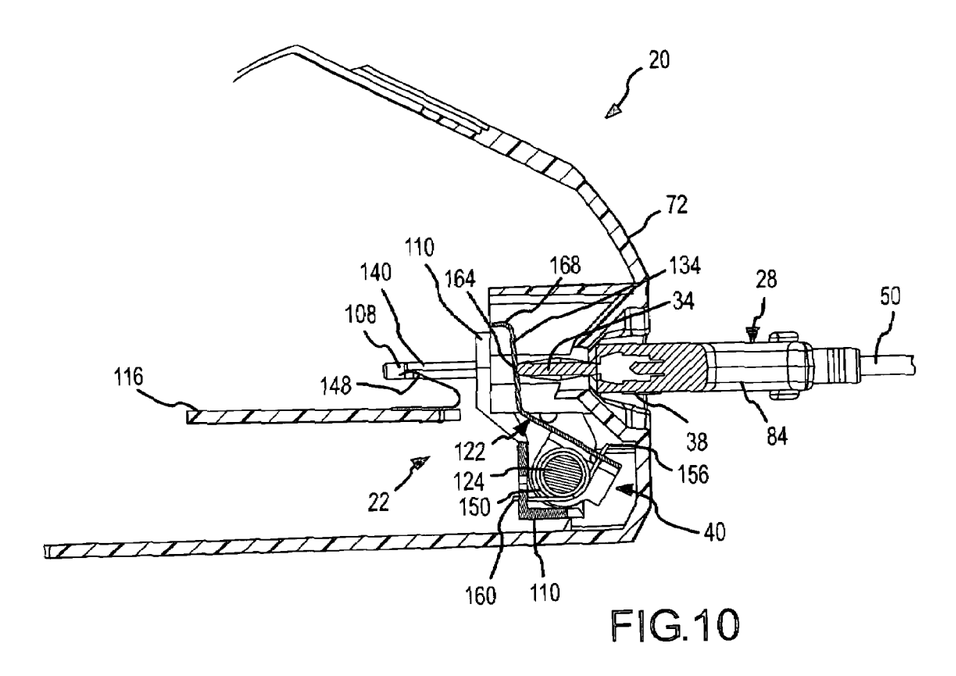
FIG. 10 is a vertical section view similar to FIG. 9, showing the insertion of an energy-conducting prong of the three-prong electrical connector into the receptacle and contact assembly, in the manner illustrated in FIG. 3.
Figure 11:
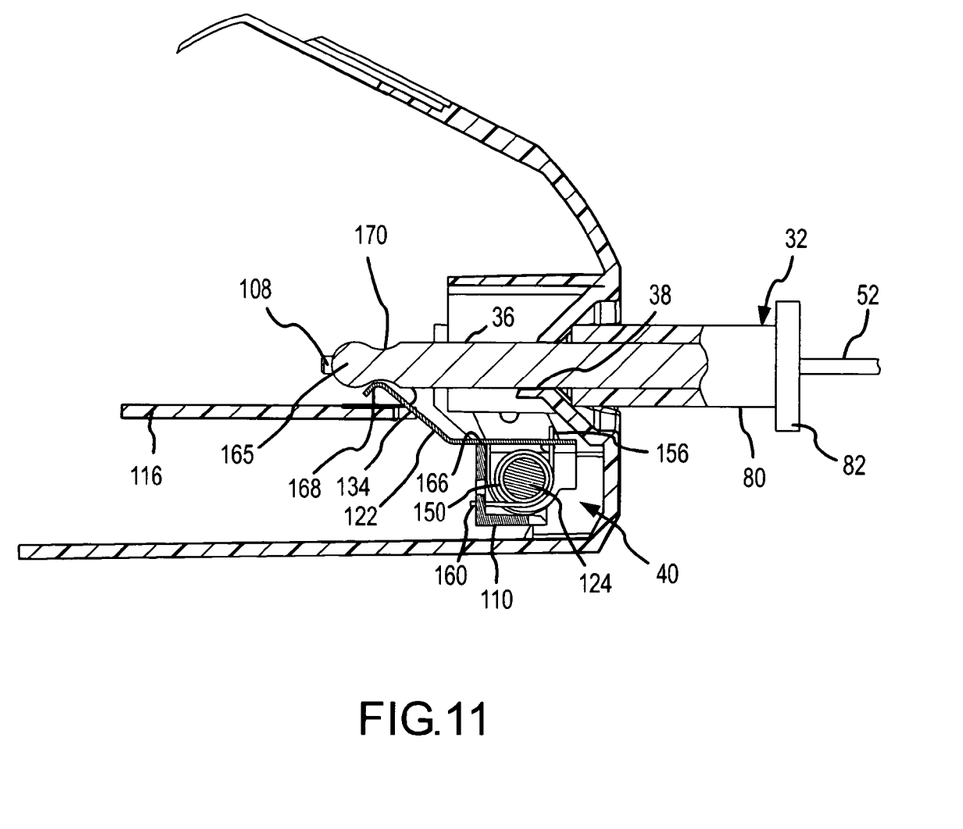
FIG. 11 is a vertical section view similar to FIG. 9, showing the insertion of an energy-conducting prong of the single-prong electrical connector into the receptacle and contact assembly, in the manner illustrated in FIG. 4.

An electrosurgical generator 20 which incorporates an integrated three-port receptacle 22 in accordance with the present invention is shown in FIG. 1. The electrosurgical generator 20 generates electrosurgical energy which is applied to the tissue of a patient during surgery by either a finger-switched electrosurgical instrument or accessory 24 or a foot-switched electrosurgical instrument or accessory 26. The finger-switched accessory 24 is connected to the electrosurgical generator 20 by inserting a three-prong electrical connector 28 into three ports of the three-port receptacle 22 (FIGS. 3 and 10). The foot-switched accessory 26 is connected to the generator 20 by inserting a single-prong electrical connector 32 into one of the ports of the three-port receptacle 22 (FIGS. 4 and 11).

An energy-conducting prong 34 of the three-prong electrical connector 28, or a energy-conducting prong 36 of the single-prong electrical connector 32, fits into a single energy-delivery port 38 (FIG. 2) of the three-port receptacle 22. An electrical contact assembly 40 (FIGS. 5, 6 and 7) of the three-port receptacle 22 is located behind the energy-delivery port 38 to conduct the electrical energy from the generator 20 to either one of the energy-conducting prongs 34 or 36 inserted in the energy-delivery port 38 (FIGS. 10 and 11).

The finger-switched accessory 24 and the foot-switched accessory 26 each include a handpiece 42 and 44 from which active electrodes 46 and 48 extend, respectively. The electrical energy is conducted from the energy-conducting prongs 34 and 36 through cables 50 and 52 to the active electrodes 46 and 48 of the accessories 24 and 26, respectively. The surgeon holds one of the handpieces 42 or 44 to manipulate the active electrode 46 or 48 at the surgical site when performing the surgical procedure.

The delivery of electrosurgical energy to the active electrode 46 of the finger-switched accessory 24 is controlled by depressing one of two finger-activated switches 54 or 56 on the handpiece 42. Depressing the switches 54 or 56 delivers generator activation signals through the cable 50 to control prongs 58 and 60 of the three-prong electrical connector 28. The control prongs 58 and 60 fit within control ports 62 and 64, respectively, of the three-port receptacle 22. The electrosurgical generator 20 responds to an activation signal on one control prong 58 or 60 by delivering electrosurgical energy which cuts the tissue, and responds to the activation signal on the other control prong 58 or 60 by delivering electrosurgical energy which coagulates the tissue. The electrosurgical energy is conducted through the electrical contact assembly 40 to the energy-conducting prong 34 which has been inserted in the energy-delivery port 38. In this manner, depression of the switches 54 and 56 on the handpiece 42 controls the delivery of electrosurgical energy through the energy-conducting prong 34 of the three-prong electrical connector 28 to the active electrode 46 of the finger-switched accessory 24.

The delivery of electrosurgical energy to the active electrode 48 of the foot-switched accessory 26 is controlled by depressing a foot switch 66. The foot switch 66 is connected by a cable 68 and an electrical connector 70 into a receptacle on a rear panel (neither shown) of the electrosurgical generator 20. Depressing the foot switch 66 supplies an activation signal through the cable 68 and connector 70 and causes the generator 20 to deliver electrosurgical energy through the electrical contact assembly 40 to the energy-conducting prong 36 of the single-prong electrical connector 32 to the foot-switched accessory 26. The electrosurgical energy is conducted through the cable 52 to the active electrode 48. The type of electrosurgical energy delivered, from the active electrode 48 of the foot-switched accessory 26, i.e. for cutting, coagulating or simultaneously cutting or coagulating, is selected from the controls on a front panel 72 of the electrosurgical generator 20. The cable 52 is shown in FIGS. 1, 4 and 10 is permanently connected to the energy-conducting prong 36, although it can also be connected to the energy-conducting prong 36 with an adaptor (not shown), which is inserted into the energy-delivery port 38 with the energy-conducting prong 36 inserted into the adapter.

Figure 2:
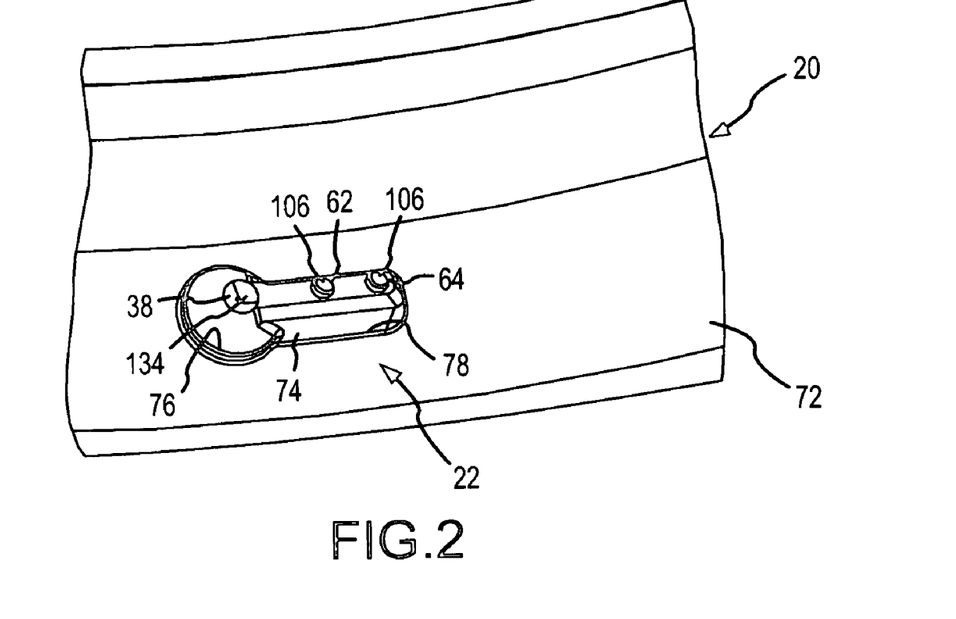
FIG. 2 is an enlarged front perspective view of the integrated three-port receptacle of the electrosurgical generator shown in FIG. 1.

The three-port receptacle 22, shown in FIG. 2, includes a recess 74 which indents rearwardly from the front panel 72 toward the interior of the generator 20. The front panel 72 is typically formed from electrically nonconductive material such as plastic, and the recess 74 is preferably integrally formed with the front panel 72. The recess 74 includes a cylindrical portion 76 which surrounds the energy-delivery port 38. The recess 74 also includes a rectangular portion 78 which extends laterally and horizontally from the cylindrical portion 76 and encompasses the control ports 62 and 64.

The diameter of the cylindrical portion 76 is greater than the transverse dimension of an insulating body 80 (FIGS. 1 and 4) of the single-prong electrical connector 32. The cylindrical portion 76 therefore provides adequate space to receive the inner portion of the insulating body 80 when the energy-conducting prong 36 is inserted into the energy-delivery port 38. An outer end portion of the insulating body 80 is formed in the shape of an annular flange 82 (FIGS. 1 and 4) which allows the insulating body 80 to be gripped when connecting the single-prong connector 32 to the three-port receptacle 22.

The horizontal and vertical dimension of the rectangular portion 78, and the cylindrical portion 76 are slightly greater in size than a rectangularly shaped (in vertical cross-section) insulating body 84 of the three-prong electrical connector 28 (FIG. 1). The energy-conducting and control prongs 34, 58 and 60 of the three-prong electrical connector 28 extend forward from the insulating body 84 so as to fit into the energy-delivery and control ports 38, 62 and 64 respectively. An outer portion of the insulating body 84 has a geometric configuration which facilitates gripping it when connecting the three-prong connector 28 to the three-port receptacle 22 (FIG. 3).

As shown in FIG. 2, the diameter of the energy-delivery port 38 is greater than the diameter of the control ports 62 and 64. The greater diameter of the energy-delivery port 38 is necessary to accommodate the greater diameter of the energy-conducting prong 36 of the single-prong electrical connector 32 compared to the relatively smaller diameter or cross sectional size of the energy-conducting prong 34 of the three-prong electrical connector 28. The energy-conducting prong 36 is also greater in length than the length of the energy-conducting prong 34 of the three-prong electrical connector 28. Since the energy-delivery port 38 is larger than energy-conducting prong 34 and has a size adequate to accept the energy-conducting prong 36 of the single-prong electrical connector 32, either of the energy-conducting prongs 34 or 36 of the electrical connectors 28 and 32, respectively, can fit within the energy-delivery port 38.

Figure 5:
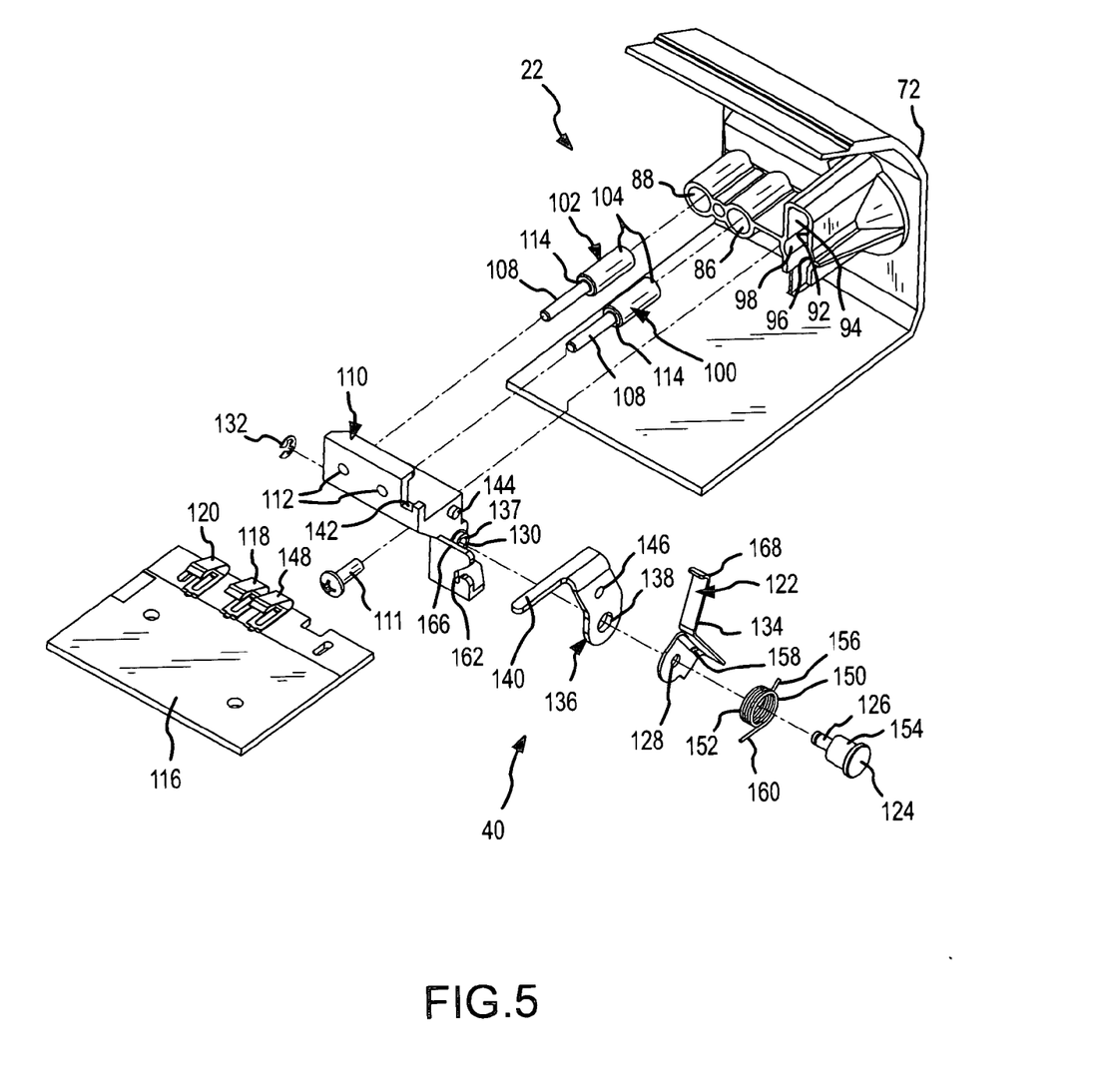
FIG. 5 is a rear exploded perspective view of the integrated three-port receptacle shown in FIGS. 1-4.

Cylindrical sleeves 86 and 88 surround the control ports 62 and 64, respectively, as shown in FIG. 5. The sleeves 86 and 88 extend rearwardly from the rectangular portion 78 (FIG. 2) of the recess 74 into the interior of the electrosurgical generator 20. Preferably, the sleeves 86 and 88 are integrally formed with the front panel 72, from the same electrically insulating material of the front panel 72. The inside diameter of the sleeves 86 and 88 is slightly larger than the inside diameter of the control ports 62 and 64, thereby causing a small annular lip 90 of the front panel 72 to surround the control ports 62 and 64, as shown in FIG. 8.

Figure 8:
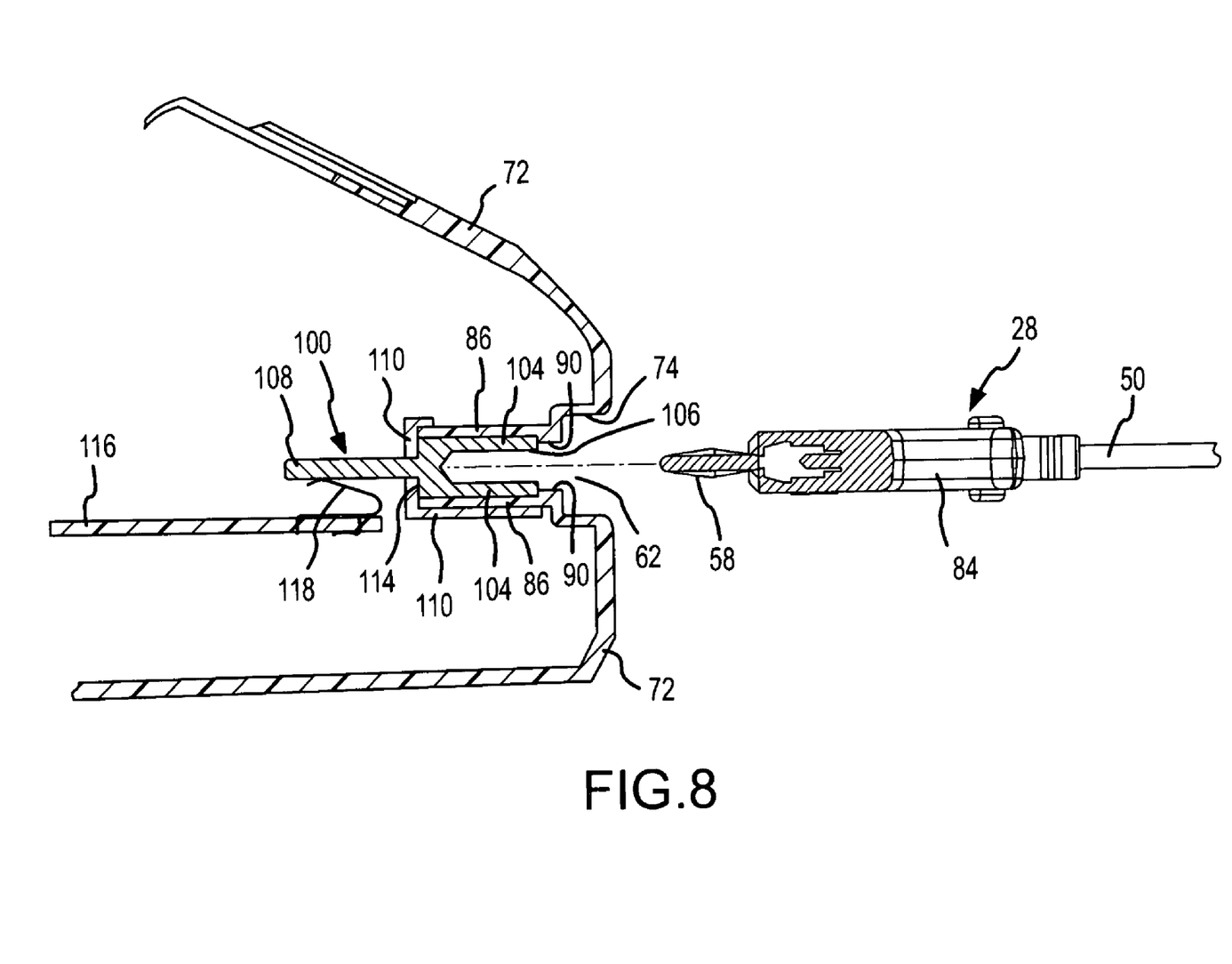
FIG. 8 is a section view taken substantially in a vertical plane through a control port and an electrical socket shown in FIG. 5 and a partially-sectioned three-prong electrical connector in an orientation to be connected to the control foot.

Electrically conductive sockets 100 and 102 are inserted into each of the cylindrical sleeves 86 and 88 from the rear of the front panel 72, as shown in FIGS. 5 and 8. Each socket 100 and 102 is formed with a forward cylindrical portion 104 which is received substantially completely within one of the cylindrical sleeves 86 and 88. The forward cylindrical portion 104 is hollow and thereby defines a cavity 106 which aligns with and opens into one of the control ports 62 or 64. Each cavity 106 of each socket 100 and 102 receives one of the control prongs 58 or 60 when the three-prong electrical connector 28 is inserted into the three-port receptacle 22. The sockets 100 and 102 can be replaced if the cavities 106 become enlarged through use. Replacing the sockets 100 and 102 ensures a continued secure connection between the control prongs 58 and 60 and the receptacle 22 even after prolonged use.

Each socket 100 and 102 also includes a smaller-diameter, solid, rearward-extending shaft portion 108 which is integral with the cylindrical portion 104. Each shaft portion 108 extends rearwardly beyond the rearward terminal end of the cylindrical sleeves 86 and 88. A support bracket 110 is secured to the front panel 72 with a fastener 111 to hold the sockets 100 and 102 in the cylindrical sleeves 86 and 88. The support bracket 110 has two cylindrical holes 112 (FIG. 5) formed in alignment with the shaft portions 108 of the sockets 100 and 102, respectively. With the support bracket 110 attached to the front panel 72, the holes 112 surround the shaft portions 108 and contact a shoulder 114 on each socket 100 and 102 formed where the shaft portion 108 extends from the larger cylindrical portion 104 of each socket 100 and 102. The support bracket 110 also contacts, or is positioned closely adjacent to, the rear edge of the cylindrical sleeves 86 and 88. The support bracket 110 prevents the sockets 100 and 102 from exiting the sleeves 86 and 88 toward the interior of the generator. The lip 90 contacts the forward terminal end of the cylindrical portion 104 to prevent each socket 100 and 102 from moving forward out of the sleeves 86 and 88. The support bracket 110 and the lip 90 trap the cylindrical portions 104 within the cylindrical sleeves 86 and 88, thereby holding the sockets 100 and 102 in the integrated three-port receptacle with their cavities 106 in alignment with the control ports 62 and 64.

Figure 6:
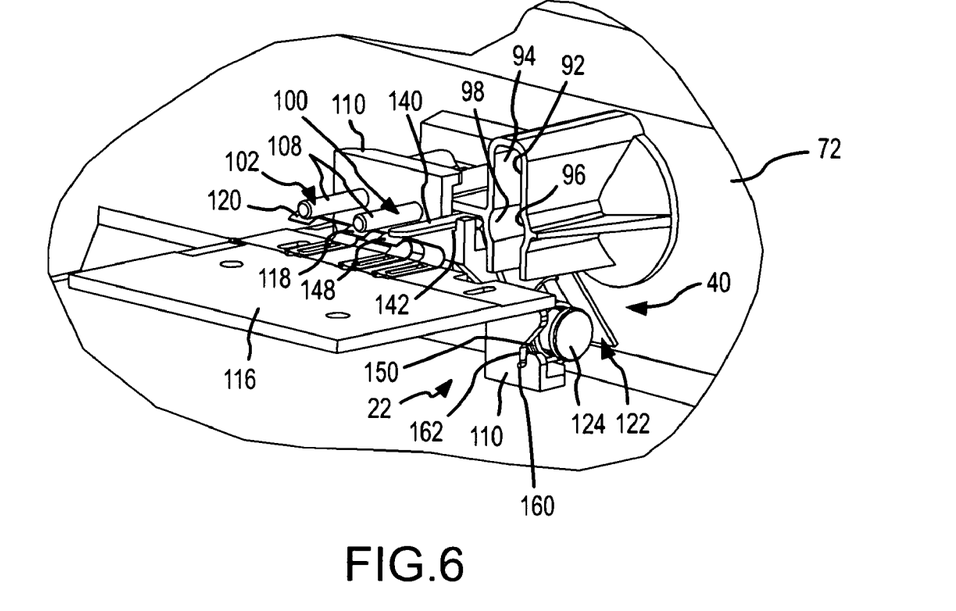
FIG. 6 is a rear perspective view of the integrated three-port receptacle shown in FIG. 5, shown in an assembled relationship and positioned in relation to a circuit board within the interior of the electrosurgical generator.
Figure 7:
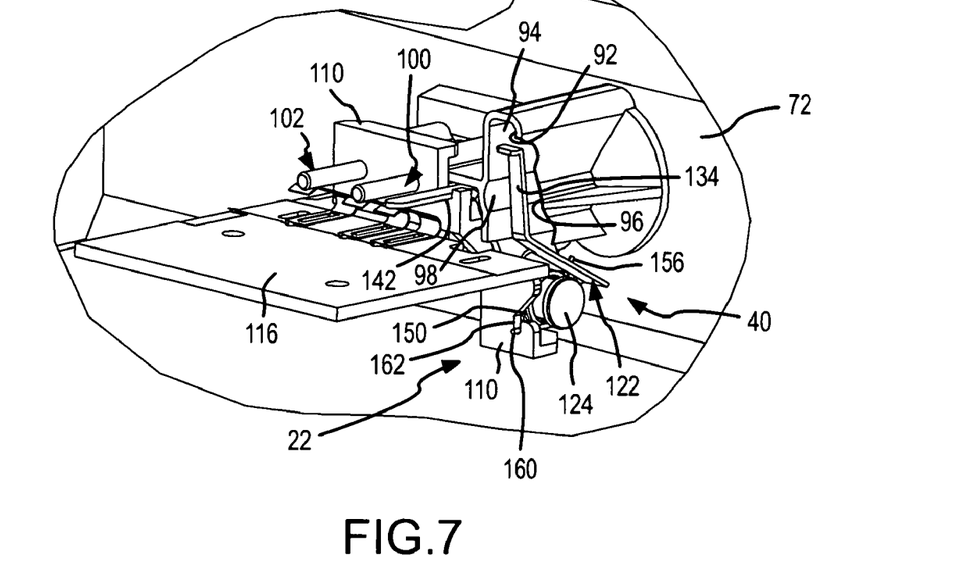
FIG. 7 is a rear perspective view similar to FIG. 6, with certain portions broken away to illustrate details of a contact assembly which contacts the energy-conducting prongs of the electrical connectors of both electrosurgical accessories shown in FIG. 1.

With the sockets 100 and 102 retained in the cylindrical sleeves 86 and 88 in the manner described, the shaft portions 108 extend rearwardly beyond the support bracket 110 and above a printed circuit board 116 located within the electrosurgical generator 20, as shown in FIGS. 6-8. The printed circuit board 116 includes electrical conductors which extend between various electrical components connected to the printed circuit (none of which are shown, but one of which included the energy delivery relay). The sockets 100 and 102 are electrically connected to the conductors of the printed circuit board 116 through resilient spring contacts 118 and 120, respectively. The spring contacts 118 and 120 are permanently attached to the printed circuit board 116 and are electrically connected to the conductors and other components of the printed circuit board 116. The spring contacts 118 and 120 resiliently deflect into electrical and mechanical contact with the shaft portions 108 of the sockets 100 and 102. Electrical conductivity is thereby established between each socket 100 and 102 and the control circuitry and other components of the printed circuit board 116. The cut and-coagulation activation signals supplied from the control prongs 58 and 60 of the three-prong electrical connector 28 are conducted through the sockets 100 and 102 and the spring contacts 118 and 120 to the conductors of the printed circuit board 116, where the logic and other electrical components of the electrosurgical generator 20 recognize and respond to those activation signals to cause the generator to deliver electrosurgical energy through the energy delivery port 38 to the energy-conducting prong 34.

A pair of laterally separated and vertically extending walls 92 and 94 extend rearwardly from the cylindrical portion 76 of the recess 74 into the interior of the electrosurgical generator 20, as shown in FIGS. 5-7. Opposing guide channels 96 and 98 are formed in the walls 92 and 94 in alignment with the energy-delivery port 38. The semicircular guide channels 96 and 98 have a curvature slightly larger than the outside cylindrical curvature of the energy-conducting prong 36 of the single-prong electrical connector 32, to permit the energy-conducting prong 36 of the connector 32 to extend into, along and between the guide channels 96 and 98 when the energy-conducting prong 36 of the single-prong electrical connector 32 is inserted in the energy-conducting port 38 of the three-port receptacle 22.

An energy-delivery electrode 122 of the contact assembly 40 conducts the electrosurgical energy from the generator 20 to either the energy-conducting prong 34 of the three-prong electrical connector 28 which has been inserted into the energy-delivery port 38 or to the energy-conducting prong 36 of the single-prong electrical connector 32 which has been inserted into the energy-delivery port 38.

A pivot pin 124 pivotally connects the energy-delivery electrode 122 to the support bracket 110. A shank portion 126 of the pivot pin 124 extends through a pivot hole 128 in the energy-delivery electrode 122 and through a hole 130 in the support bracket 110. The pivot pin 124 is secured to the support bracket 110 by connecting a snap ring 132 to the end of the shank portion 126 after it has been extended through the hole 130. Positioned in this manner, a prong contact arm portion 134 of the energy-delivery electrode 122 is located in the space between the walls 92 and 94. Pivoting movement of the energy-delivery electrode 122 about the pivot pin 124 causes the prong contact arm portion 134 to move within the space between the walls 92 and 94 (FIGS. 6, 7 and 9-11). Since the walls 92 and 94 extend rearwardly on opposite sides of the energy-delivery port 38, the prong contact arm portion 134 is located rearwardly in alignment with the energy-delivery port 38.

A transfer electrode 136 contacts the energy-delivery electrode 122 and is connected to the support bracket 110 by the pivot pin 124, as shown in FIG. 5. The transfer electrode 136 includes a hole 138 through which a sleeve 137 of the support bracket 110 extends. The shank portion 126 of the pivot pin 124 extends through the sleeve 137. The transfer electrode 136 is therefore positioned between the energy-delivery electrode 122 and the support bracket 110. The energy-delivery electrode 122 and the energy-transfer electrode 136 are positioned in an axially contacting and adjoining relationship along the shank portion 126 of the pivot pin 124 while electrically contacting one another, as a result of their common connection by the pivot pin 124 and the sleeve 137 to the support bracket 110.

A connector arm portion 140 (FIG. 5) of the transfer electrode 136 extends rearwardly through a notch 142 in the support bracket 110, as shown in FIG. 5. A stud 144 extends from the support bracket 110 and into a hole 146 formed in the transfer electrode 136 when the transfer electrode 136 is attached to the support bracket 110 by the pivot pin 124. Retained to the support bracket 110 in this manner, the transfer electrode 136 does not pivot relative to the support bracket 110. The connector arm portion 140 extends in a substantially parallel relationship with the shaft portions 108 of the sockets 100 and 102.

The connector arm portion 140 is contacted by a spring contact 148 which is attached to the printed circuit board 116. The electrosurgical energy from the electrosurgical generator is supplied through a conductor (not shown) on the printed circuit board 116 to the spring contact 148. The electrosurgical energy is conducted through the spring contact 148 to the connector arm portion 140 of the transfer electrode 136. The energy flows from the transfer electrode 136 to the electrically-connected energy-delivery electrode 122 and from there to the energy-conducting prong 34 or 36 of the electrical connector 28 or 32, respectively, which has been inserted into the energy-delivery port 38.

Figure 9:
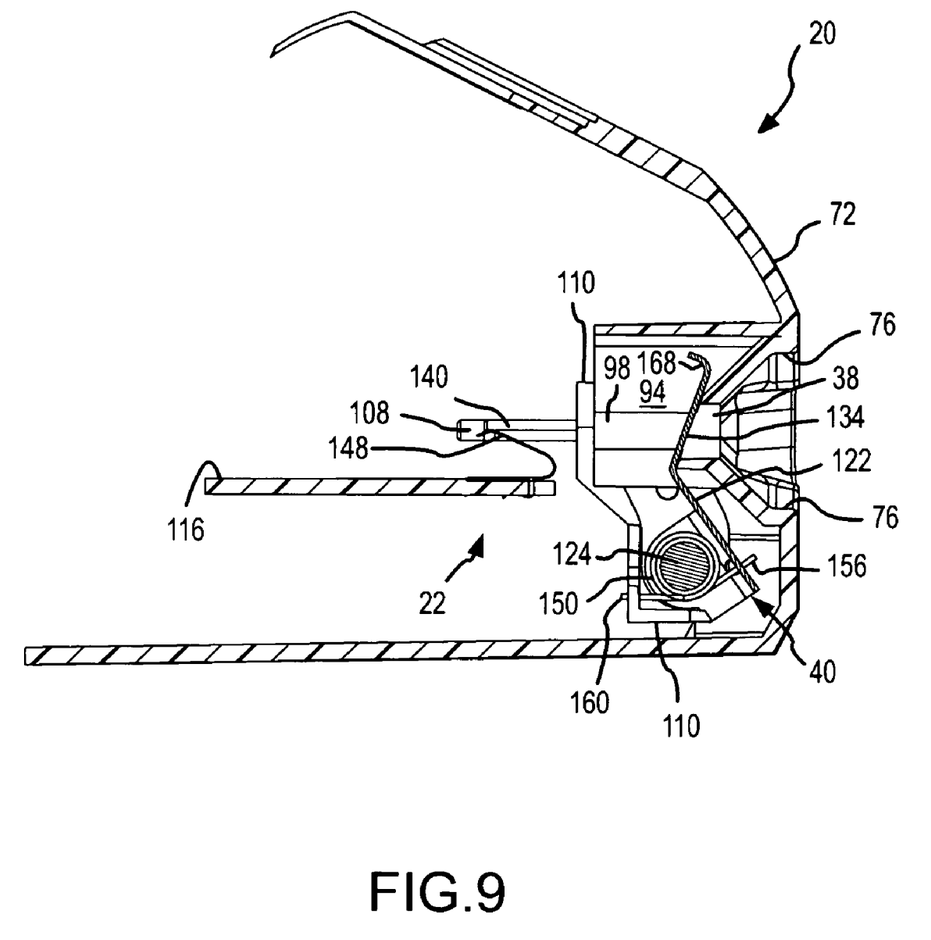
FIG. 9 is a section view taken substantially in a vertical plane through an energy-delivery port and the contact assembly shown in FIG. 7.

The prong contact arm portion 134 of the energy-delivery electrode 122 is biased into a normal pivoted position (shown in FIG. 9) adjacent to the energy-delivery port 38 by a pivot bias spring 150, shown in FIG. 5. The pivot bias spring 150 is a torsion-type coil spring with a center coil 152 that extends around an enlarged end portion 154 of the pivot pin 124 on the side of the energy-delivery electrode 122 axially opposite from the transfer electrode 136. An end 156 of the pivot bias spring 150 extends from the center coil 152 and is inserted into a hole 158 in the energy-delivery electrode 122. Another end 160 of the pivot bias spring 150 extends from the center coil 152 into a slot 162 in the support bracket 110. As a result, the bias force supplied by the spring 150 tends to pivot the energy-delivery electrode 122 clockwise relative to the transfer electrode 136, as shown in the orientation of FIGS. 6-11. With this bias force on the energy-delivery electrode 122, the prong contact arm portion 134 is biased into a normal position located immediately behind the energy-delivery port 38 (FIG. 9). The center coil 152 of the spring 150 also biases the energy-delivery electrode 122 in contact with the transfer electrode 136, thereby assuring good electrical connection between the electrodes 122 and 136.

When the three-prong electrical connector 28 of a finger-switched accessory 24 is connected to the generator 20, as shown in FIGS. 3 and 10, the energy-conducting prong 34 extends through the energy-delivery port 38 and a distal end portion 164 of the energy-conducting prong 34 contacts the prong contact arm portion 134. The insertion of the energy-conducting prong 34 pivots the energy-delivery electrode 122 and the prong contact arm portion 134 counterclockwise, is apparent by comparing FIGS. 9 and 10. The end 156 of the pivot bias spring 150 moves counterclockwise around the pivot pin 124, increasing the tension force from the bias spring 150 and causing the prong contact arm portion 134 to firmly mechanically contact the distal end of the energy-conducting prong 34.

When the three-prong connector 28 is fully inserted in the three-port receptacle 22, as shown in FIGS. 3, 8 and 10, the frictional insertion of the control prongs 58 and 60 into the cavities 106 of the sockets 100 and 102 of the control ports 62 and 64 mechanically holds the three-prong electrical connector 28 in the three-port receptacle 22. The prongs 34, 58 and 60 are slightly compressible in a transverse dimension, as is conventional, and the compression of the prongs 58 and 60 within the cavities 106 of the sockets 100 and 102 is sufficient to maintain the three-prong electrical connector 28 connected to the generator 20 while withstanding the bias force from the prong contact arm portion 134 against the distal end 164 of the energy-conducting prong 34. The frictional maintenance of the control prongs 58 and 60 in the cavities 106 of the sockets 100 and 102 assures that a reliable electrical connection will be established between the control prongs 58 and 60 and the sockets 100 and 102, respectively, as well as between the prong contact arm portion 134 and the energy-conducting prong 34. If the control prongs 58 and 60 are not inserted sufficiently into the cavities 106 of the sockets 100 and 102, the entire three-prong electrical connector 28 will be removed from the three-port receptacle 22 by the pivot force of the prong contact arm position 134 of the energy-delivery electrode 122. The three-prong electrical connector 28 is disconnected from a secure connection in the three-port receptacle 22 by gripping the insulating body 84 and withdrawing the prongs 34, 58 and 60 from the energy-delivery port 38 and the cavities 106 within the sockets 100 and 102 of the control ports 62 and 64, respectively.

When the single-prong electrical connector 32 of the foot-switched accessory 26 is connected to the generator 20, as shown in FIGS. 4 and 11, the energy-conducting prong 36 extends through the energy-delivery port 38 and contacts the prong contact arm portion 134. The energy-conducting prong 36 enters the energy-delivery port 38 and moves longitudinally inward along the guide channels 96 and 98 formed in the walls 92 and 94, respectively (FIG. 5). The guide channels 96 and 98 ensure that the energy-conducting prong 36 extends along an established path so that the energy-conducting prong 36 contacts the prong contact arm portion 134 of the energy-delivery electrode 122. The energy-conducting prong 36 has a distal end 165 which contacts the prong contact arm portion 134 and pivots the prong contact arm portion 134 and the energy-delivery electrode 122 counterclockwise (FIG. 11) against the bias force of the pivot bias 150, as the prong 36 is inserted into the energy-delivery port 38.

The energy-delivery electrode 122 continues to pivot as the energy-conducting prong 36 is inserted until the prong contact arm portion 134 contacts a stop extension 166 of the support bracket 110 (FIG. 5). The energy-delivery electrode 122 is prevented from further pivoting around the pivot pin 124 when the prong contact arm portion 134 contacts the stop extension 166. Further insertion of the energy-conducting prong 36 causes the contact arm portion 134 to bend resiliently until a curved outer end portion 168 of the prong contact arm portion 134 engages an annular indention 170 at the distal end 165 of the energy-conducting prong 36.

Retention force is created by the resilient deformation of the prong contact arm portion 134 and the insertion of the curved end portion 168 into the annular indention 170. The retention force is sufficient to hold the single-prong connector 32 in the energy-delivery port 38 of the three-port receptacle 22, and to resist its accidental or unintentional withdrawal. Furthermore, if the single-prong electrical connector 32 is not fully inserted, the force of the deformed and pivoted prong contact arm portion 134 and the pivot bias spring 150 will move the energy-conducting prong 36 out of the energy-delivery port 38. In this manner, the single-prong electrical connector 32 will be fully inserted and adequately connected electrically and mechanically to the electrosurgical generator 20 before the foot-switched accessory 26 is used. Of course, the single-prong electrical connector 32 is disconnected from the three-port receptacle 22 by gripping the insulating body 80 and the flange 82, and withdrawing the energy-conducting prong 36 from the energy-delivery port 38. The withdrawal force applied on the body 80 is sufficient to deflect the curved end 168 of the prong contact area portion 134 out of the annular indentation 170, thereby allowing the single-prong electrical connector 32 to be removed from the energy-delivery port 38 while the energy-delivery electrode 122 returns to its normal biased position (FIG. 9).

By accepting the relatively smaller energy-conducting prong 34 of the three-prong connector 28 and the relatively larger energy-conducting prong 36 of the single-prong electrical connector 32, the integrated three-port receptacle 22 is able to supply electrosurgical energy to both a finger-switched accessory 24 as well as to a foot-switched accessory 26. Consequently, the three-port receptacle 22 will connect to and supply energy to both standard configurations of electrosurgical accessories.

The integrated three-port receptacle 22 has a decreased size in comparison to having separate dedicated receptacles for finger-switched accessories and for foot switched accessories. The contact assembly 40 of the three-port receptacle 22 also has a reduced size compared to the electrical components necessary for previous four-port receptacles. The reduced size of the integrated three-port receptacle 22 consumes less valuable space on the front panel of the electrosurgical generator in comparison to separate dedicated receptacles for finger-switched accessories and for foot-switched accessories. The reduced size of the single contact assembly 40 consumes less of the valuable space inside of the generator in comparison to previous four-port receptacles, because previous four-port receptacles require a separate electrical contact assembly for each of its two energy-delivery ports as well as a separate energy-delivery relay for each of its two energy-delivery ports. The reduced size of the integrated three-port receptacle 22 therefore allows the electrosurgical generator to use multiple integrated three-port receptacles 22 while still utilizing the space of the front panel efficiently.

While this invention has been described in detail in the specification and illustrated in detail in the drawings with reference to a preferred embodiment, various changes or modifications may be made without departing from the scope of the invention. Therefore, it is intended that the invention not necessarily be limited to the particular embodiment and details disclosed in the specification and shown in the drawings, but that the invention include all embodiments, modifications and changes as may come within the scope of the following claims.

What is claimed is:

1. An integrated three-port receptacle for alternatively electrically connecting a three-prong electrical connector of a finger-switched electrosurgical accessory and a single-prong electrical connector of a foot-switched electrosurgical accessory to an electrosurgical generator, the three-prong electrical connector having two control prongs and a single energy-conducting prong for conducting electrosurgical energy from the electrosurgical generator to the finger-switched electrosurgical accessory, the single-prong electrical connector having a single energy-conducting prong for conducting electrosurgical energy from the electrosurgical generator to the foot-switched electrosurgical accessory, the receptacle comprising:

a first control port for receiving and electrically connecting to one of the control prongs of the three-prong electrical connector when inserted in the first control port;

a second control port for receiving and electrically connecting the other one of the control prongs of the three-prong electrical connector when inserted in the second control port;

an energy-delivery port for receiving the energy-conducting prong of the single-prong electrical connector when inserted in the energy-delivery port and for receiving the energy-conducting prong of the three-prong electrical connector when the energy-conducting prong and the two control prongs of the three-prong electrical connector are received in the energy-delivery and first and second control ports, respectively; and an electrical contact positioned relative to the energy-delivery port for electrically contacting the energy-conducting prong of the three-prong electrical connector and the energy-conducting prong of the single-prong electrical connector when either energy-conducting prong is received in the energy-delivery port, the electrical contact conducting the electrosurgical energy from the electrosurgical generator to the energy-conducting prong received in the energy-delivery port.

2. An integrated three-port receptacle as defined in claim 1, wherein:

the energy-conducting prong of the single-prong electrical connector is larger in a transverse dimension than the energy-conducting prong of the three-prong electrical connector is in a transverse dimension.

3. An integrated three-port receptacle as defined in claim 2, wherein:

the energy-delivery port has a fixed size which provides a relatively lesser clearance relative to the energy-conducting prong of the single-prong electrical connector and which provides a relatively greater clearance relative to the energy-conducting prong of the three-prong electrical connector; and the first and second control ports frictionally retain the control prongs of the three-prong electrical connector to maintain the energy-conducting prong of the three-prong electrical connector within the energy-delivery port.

4. An integrated three-port receptacle as defined in claim 3, wherein:

the electrical contact comprises an energy-delivery electrode which electrically contacts the energy-conducting prong of either one of the three-prong electrical connector and the single-prong connector when inserted in the energy-delivery port.

5. An integrated three-port receptacle as defined in claim 4, wherein:
the energy-delivery electrode includes an elongated contact arm portion which pivots relative to the energy-delivery port to move into contact with the energy-conducting prong of either one of the single-prong electrical connector and the three-prong electrical connector.

6. An integrated three-port receptacle as defined in claim 5, wherein:
the energy-conducting prong of the three-prong electrical connector has a distal end that is electrically conductive; and
the contact arm portion of the energy-delivery electrode moves into contact with the distal end of the energy-conducting prong.

7. An integrated three-port receptacle as defined in claim 5, wherein:
the energy-conducting prong of the single-prong electrical connector has a distal end with a side wall that is electrically conductive; and
the contact arm portion of the energy-delivery electrode moves into contact with the side wall of the distal end of the energy-conducting prong of the single-prong electrical connector.

8. An integrated three-port receptacle as defined in claim 7, wherein:
the energy-conducting prong of the single-prong electrical connector has a longitudinal dimension which is greater than a longitudinal dimension of the energy-conducting prong of the three-prong electrical connector;
the side wall of the distal end of the energy-conducting prong of the single-prong electrical connector includes a circumferential indention; and
the contact arm portion includes an end portion which moves into the indention when the energy-conducting prong of the single-prong electrical connector is inserted completely into the energy-delivery port.

9. An integrated three-port receptacle as defined in claim 8, wherein:
the movement of the end portion of the contact arm portion into the indention frictionally retains the energy-conducting prong of the single-prong electrical connector within the energy-delivery port.

10. An integrated three-port receptacle as defined in claim 9, wherein:
the end portion of the contact arm portion transfers the electrosurgical energy from the energy-delivery electrode to the energy-conducting prong of the single-prong electrical connector.

11. An integrated three-port receptacle as defined in claim 9, wherein:
the contact arm portion is resiliently deflectable;
the contact arm portion ceases pivoting movement before the end portion of the contact arm portion moves into the indention as the energy-conducting prong of the single-prong electrical connector is inserted completely into the energy-delivery port; and
the end portion of the contact arm portion moves into the indention from resilient deflection of the contact arm portion after the contact arm portion ceases pivoting movement and due to continued insertion of the energy-conducting prong of the single-prong electrical connector into the energy-delivery port.

12. An integrated three-port receptacle as defined in claim 11, further comprising:
a stop for contacting the contact arm portion to cease pivoting movement of the contact arm portion, the stop causing the contact arm portion to deflect resiliently after the pivoting movement is ceased;
the energy-conducting prong of the three-prong electrical connector has a distal end that is electrically conductive;
the contact arm portion of the energy-delivery electrode pivots into contact with the distal end of the energy-conducting prong of either one of the three-prong electrical connector and the single-prong electrical connector; and
the stop allows the contact arm portion to pivot into contact with the distal end portion of the energy-conducting prong of the three-prong electrical connector and causes the contact arm portion to deflect resiliently before the end portion of the contact arm portion moves into the indention.

13. An integrated three-port receptacle as defined in claim 5, further comprising:
a bias spring connected to the energy-delivery electrode for biasing the contact arm portion into a normal position adjacent the energy delivery port, the bias spring permitting pivotal movement of the contact arm portion to move into contact with the energy-conducting prong of either one of the three-prong electrical connector and the single-prong electrical connector when inserted into the energy-delivery port, the bias spring further maintaining contact of the contact arm portion with the energy-conducting prong of the three-prong electrical connector when inserted into the energy-delivery port.

14. An integrated three-port receptacle as defined in claim 4, further comprising:
a transfer electrode electrically connected to the energy-delivery electrode, the transfer electrode including a connector arm portion;
a circuit board located within the electrosurgical generator having a portion which is adjacent to the connector arm portion; and
a contact member connected to the circuit board and contacting the connector arm portion for transferring the electrosurgical energy from the circuit board to the connector arm portion.

15. An integrated three-port receptacle as defined in claim 14, wherein:
the connector arm portion remains substantially stationary as the contact arm portion pivots.

16. An integrated three-port receptacle as defined in claim 15, further comprising:
a pivot pin connected to the energy-delivery electrode and about which the contact arm portion pivots; and
wherein:
the pivot pin extends through the transfer electrode;
the connector arm portion and the transfer electrode remaining substantially stationary during pivoting of the energy-delivery electrode; and
the energy-delivery electrode pivots relative to the connector arm portion while in contact the transfer electrode when the energy-conducting prong of either one of the three-prong electrical connector and the single-prong electrical connector is inserted within the energy delivery port.

17. An integrated three-port receptacle as defined in claim 16, further comprising:
an electrically conductive socket within each of the first and second control ports, each conductive socket having an internal cavity within which to receive one of the control prongs of the three-prong electrical connector, each conductive socket further having a shaft portion extending from the conductive socket portion; and wherein:

the circuit board further includes a portion which is adjacent to the shaft portions of the conductive sockets within each of the first and second control ports; and the circuit board further includes contact members contacting the shaft portions of the conductive sockets for transferring signals between the control prongs of the three-prong electrical connector and the circuit board.

18. An integrated three-port receptacle as defined in claim 17, wherein:

the contact members are resilient and deflectable into contact with the respective shaft portions of the conductive sockets and the connector arm portion of the transfer electrode.

19. An integrated three-port receptacle as defined in claim 17, wherein:

each conductive socket includes a cylindrical portion within which the cavity is located;

the shaft portion extends from the cylindrical portion at a shoulder at which the cylindrical portion transitions to the shaft portion; and further comprising:

a cylindrical sleeve which extends rearward from each control port and within which the cylindrical portion of each conductive socket is received;

a support bracket having holes therein within which to receive the shaft portions of the conductive sockets and to contact the shoulders of the conductive sockets to retain the conductive sockets within the cylindrical sleeves and relative to the control ports; and wherein:

the pivot pin is connected to the support bracket;

the support bracket is formed substantially from electrically nonconductive material; and the shaft portions of the conductive sockets and the connector arm portion of the transfer electrode extend generally parallel to one another and extend over the circuit board.

20. A method of alternatively electrically connecting a finger-switched electrosurgical accessory and a foot-switched electrosurgical accessory to an electrosurgical generator by connecting a three-prong electrical connector and a single-prong electrical connector to the electrosurgical generator, respectively, the method comprising:

inserting an energy-conducting prong of the three-prong electrical connector into an energy-delivery port of the electrosurgical generator and inserting two control prongs of the three-prong electrical connector into control ports of the electrosurgical generator to electrically connect the finger-switched electrosurgical accessory to the electrosurgical generator;

retaining the energy-conducting prong of the three-prong electrical connector in the energy-delivery port by frictionally retaining the two control prongs of the three-prong electrical connector in the control ports;

inserting the energy-conducting prong of the single-prong electrical connector into the energy-delivery port to electrically connect the foot-switched electrosurgical accessory to the electrosurgical generator; and retaining the energy-conducting prong of the single-prong electrical connector in the energy-delivery port by frictional retention of energy-conducting prong of the single-prong electrical connector in the energy-delivery port.

21. A method as defined in claim 20, wherein the energy-conducting prong of the single-prong electrical connector is larger in a transverse dimension than the energy-conducting prong of the three-prong electrical connector is in a transverse dimension, and the energy-delivery port has a fixed size which provides a relatively lesser clearance relative to the energy-conducting prong of the single-prong electrical connector and which provides a relatively greater clearance relative to the energy-conducting prong of the three-prong electrical connector.

22. A method as defined in claim 21, further comprising:

contacting the energy-conducting prong of either one of the three-prong electrical connector and the single-prong connector when inserted in the energy-delivery port to transfer electrosurgical energy from the electrosurgical generator to the finger-switched electrosurgical accessory and the foot-switched electrosurgical accessory, respectively.

23. A method as defined in claim 22, wherein the energy-conducting prong of the single-prong electrical connector has a side wall, and the method further comprises:

moving an energy-delivery electrode into contact with the side wall of the energy-conducting prong of the single-prong electrical connector to transfer the electrosurgical energy to the foot-switched electrosurgical accessory.

24. A method as defined in claim 23, wherein the side wall of the distal end of the energy-conducting prong of the single-prong electrical connector includes a circumferential indention, the energy-delivery electrode includes a contact arm portion, and the contact arm portion includes an end portion, and the method further comprises:

moving the end portion of the contact arm portion into the indention when the energy-conducting prong of the single-prong electrical connector is inserted completely into the energy-delivery port to resist removal of the energy-conducting prong of the single-prong electrical connector from the energy-delivery port.

25. A method as defined in claim 24, further comprising:

resiliently deflecting the contact arm portion when the end portion of the contact arm portion is in the indention.

26. A method as defined in claim 22, wherein the energy-conducting prong of the three-prong electrical connector has a distal end, and the method further comprises:

moving an energy-delivery electrode into contact with the distal end of the energy-conducting prong of the three-prong electrical connector to transfer the electrosurgical energy to the finger-switched electrosurgical accessory.

27. A method as defined in claim 26, further comprising:

pivoting the energy-delivery electrode into contact with the distal end of the energy-conducting prong of the single-prong electrical connector.

* * * * *